(12) United States Patent
Currier et al.

(10) Patent No.: US 7,029,467 B2
(45) Date of Patent: *Apr. 18, 2006

(54) MULTIPLE LUMEN CATHETER HAVING A SOFT TIP

(75) Inventors: Clifford Currier, Aliso Viejo, CA (US); Michael Higgins, Huntington Beach, CA (US); Mark Gordon, Corona Del Mar, CA (US); Stacy Faught, Aliso Viejo, CA (US); Dean West, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 136 days.

This patent is subject to a terminal disclaimer.

(21) Appl. No.: 10/195,954

(22) Filed: Jul. 16, 2002

(65) Prior Publication Data

US 2004/0015138 A1    Jan. 22, 2004

(51) Int. Cl.
  *A61M 25/00* (2006.01)
  *A61M 5/00* (2006.01)
(52) U.S. Cl. .................. 604/525; 604/264
(58) Field of Classification Search .......... 604/48, 604/500, 506–508, 93.01, 164.01, 173, 264, 604/524, 525, 526, 527, 540–544, 533–535, 604/523; 600/481, 485–487, 309–310, 325, 600/327, 433–435, 466, 585; 607/122; 606/481, 485–487

See application file for complete search history.

(56) References Cited

U.S. PATENT DOCUMENTS 3,434,775 A    3/1969   Gosselin (Continued)

FOREIGN PATENT DOCUMENTS

EP    0 336 984 B1    4/1988

(Continued)

*Primary Examiner*—Nicholas D. Lucchesi
*Assistant Examiner*—Matthew F. DeSanto
(74) *Attorney, Agent, or Firm*—Edwards Lifesciences

(57) ABSTRACT

A multiple lumen catheter having a soft, tapered multiple lumen distal tip for insertion into a body vessel. One of the lumens is sized to pass over a guidewire such that the catheter can be inserted into the body vessel using the Seldinger technique. At least one medical implement lumen is used for placement or positioning of a biomedical sensor or other medical implement. For example, at least one optical fiber passing through the medical implement lumen may transmit and receive light at the distal tip for measuring oxygen saturation of the blood. The catheter may have a cylindrical catheter body to which the soft distal tip attaches. The soft tip reduces the possibility of vessel or tissue puncture and abrasion. The tip is constructed of a soft plastic or pliable material that yields easily when force is applied. For example, the tip may be made of a softer material than the catheter body, or if made of the same material, the tip can be configured with thinner walls or a higher air-to-material ratio cross-section. Various geometrical configurations and combinations of materials can be used to decrease the flexible resistance of the tip to an applied load. One particular useful application for the catheter of the present invention is as a central venous catheter equipped with fibers for measuring oximetry. The fibers extend to the distal end of the tip and are preferably secured therein with minimal adhesive so as to limit the stiffness added to the tip. One particular useful construction is to secure the fibers within the medical implement lumen using adhesive only along a length of between about 0.5–3.5 mm.

25 Claims, 11 Drawing Sheets

U.S. PATENT DOCUMENTS

| | | | |
|---|---|---|---|
| 3,807,390 A | | 4/1974 | Ostrowski et al. |
| 3,847,483 A | | 11/1974 | Shaw et al. |
| 4,487,475 A | | 12/1984 | Ogawa |
| 4,647,149 A | | 3/1987 | McCartney |
| 4,648,892 A | | 3/1987 | Kittrell |
| 4,695,276 A | * | 9/1987 | Shinno et al. ............. 604/533 |
| 4,718,423 A | | 1/1988 | Willis et al. |
| 4,759,378 A | | 7/1988 | Swendson et al. |
| 4,776,340 A | | 10/1988 | Moran et al. |
| 4,788,967 A | | 12/1988 | Ueda |
| 4,790,295 A | | 12/1988 | Tashiro |
| 4,795,434 A | | 1/1989 | Kujawski |
| 4,796,604 A | | 1/1989 | Kawashima |
| 4,813,400 A | | 3/1989 | Washizuka et al. |
| 4,830,013 A | | 5/1989 | Maxwell |
| 4,871,229 A | | 10/1989 | Tashiro |
| 4,911,148 A | * | 3/1990 | Sosnowski et al. ......... 600/136 |
| 4,921,483 A | * | 5/1990 | Wijay et al. ............ 604/103.1 |
| 5,047,627 A | | 9/1991 | Yim |
| 5,048,524 A | | 9/1991 | Bailey |
| 5,263,928 A | | 11/1993 | Trauthen et al. |
| 5,263,952 A | | 11/1993 | Grace et al. |
| 5,280,786 A | | 1/1994 | Wlodarczyk |
| 5,315,995 A | | 5/1994 | Rivers |
| 5,443,057 A | | 8/1995 | Elmore |
| 5,456,680 A | | 10/1995 | Taylor et al. |
| 5,466,234 A | | 11/1995 | Loeb et al. |
| 5,470,330 A | | 11/1995 | Goldenberg et al. |
| 5,542,924 A | | 8/1996 | Snoke et al. |
| 5,566,680 A | * | 10/1996 | Urion et al. ................. 600/561 |
| 5,601,087 A | | 2/1997 | Gunderson |
| 5,665,051 A | | 9/1997 | Quick et al. |
| 5,673,694 A | | 10/1997 | Rivers |
| 5,702,368 A | | 12/1997 | Stevens et al. |
| 5,788,647 A | | 8/1998 | Eggers |
| 5,807,261 A | | 9/1998 | Benaron |
| 5,902,247 A | | 5/1999 | Coe |
| 5,995,208 A | | 11/1999 | Sarge |
| 6,033,398 A | * | 3/2000 | Farley et al. ................. 606/27 |
| 6,196,966 B1 | | 3/2001 | Kerin et al. |
| 6,210,362 B1 | | 4/2001 | Ponzi |
| 6,352,531 B1 | | 3/2002 | O'Connor et al. |
| 6,374,476 B1 | | 4/2002 | Ponzi et al. |
| 6,520,934 B1 | | 2/2003 | Lee et al. |

FOREIGN PATENT DOCUMENTS

| | | |
|---|---|---|
| EP | 0 336 985 B1 | 4/1988 |
| EP | 0 311 458 | 4/1989 |
| EP | 338149 A1 | 10/1989 |
| EP | 0 514 913 | 11/1992 |
| EP | 0 571 184 A2 | 5/1993 |
| EP | 0 575 732 B1 | 5/1993 |
| GB | 2210560 A | 10/1987 |
| WO | WO 97/06726 A1 | 2/1997 |
| WO | WO 97/13452 A1 | 4/1997 |

* cited by examiner

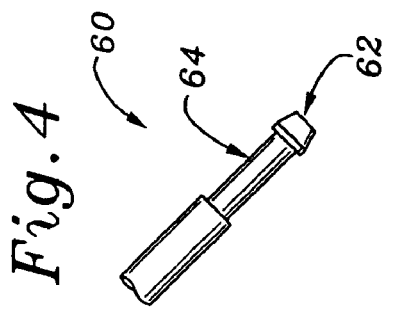
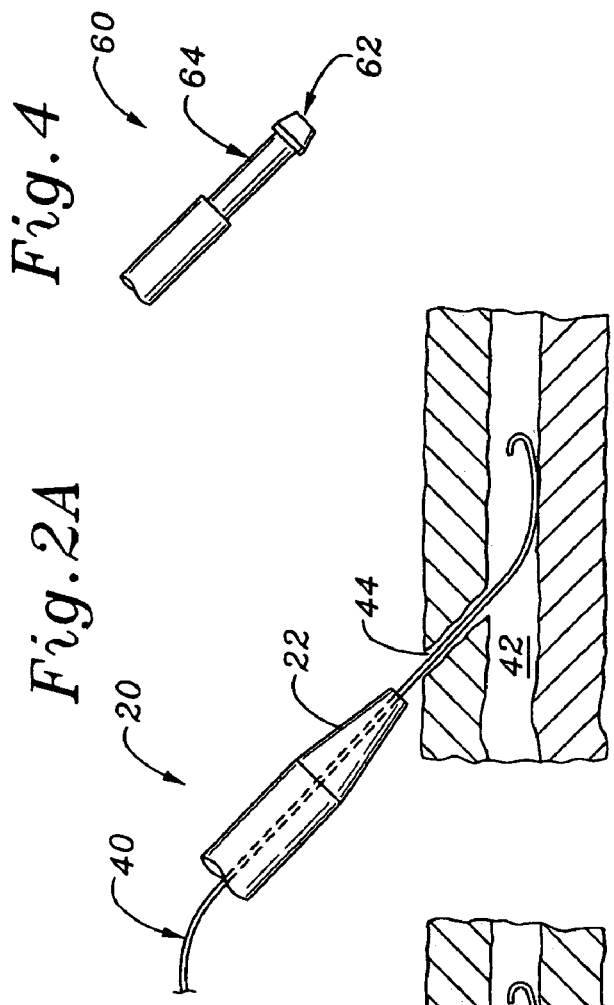
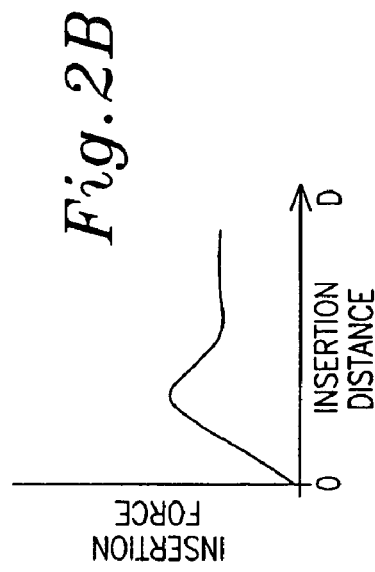
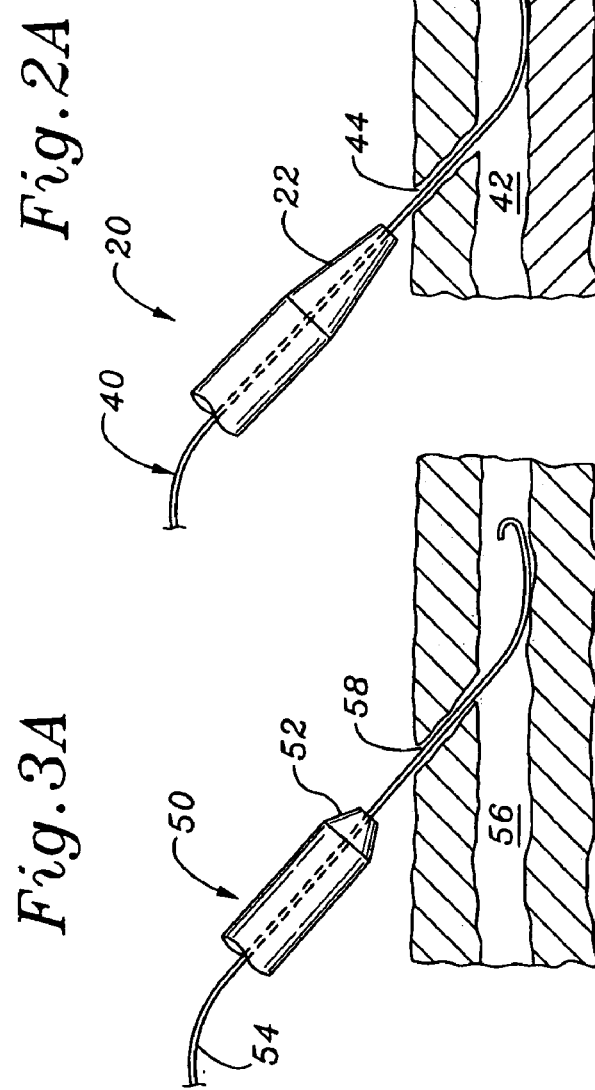
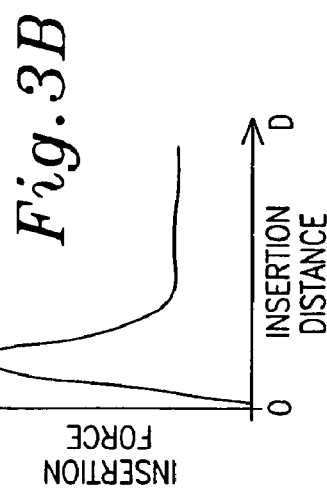

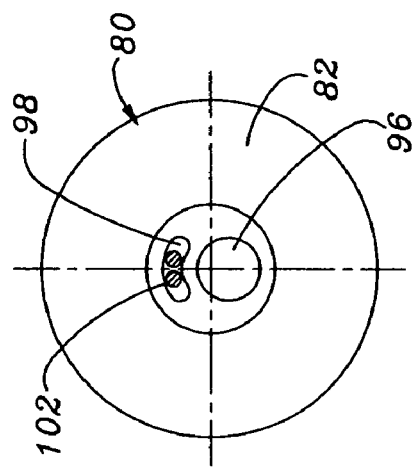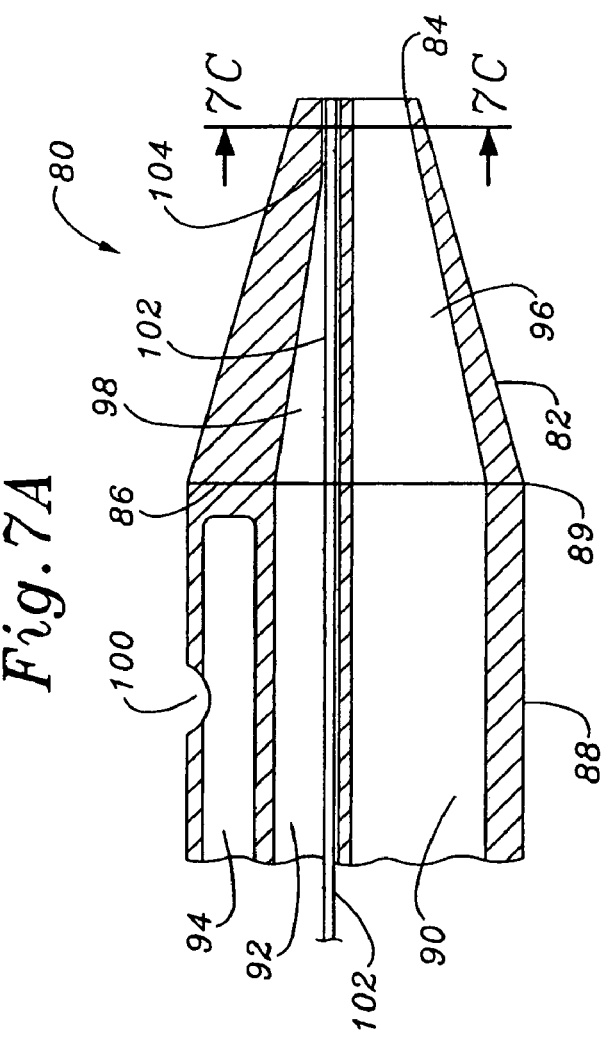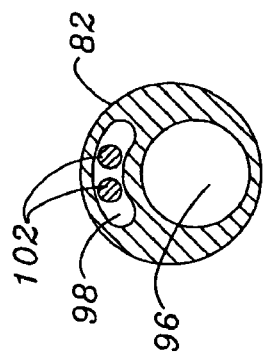

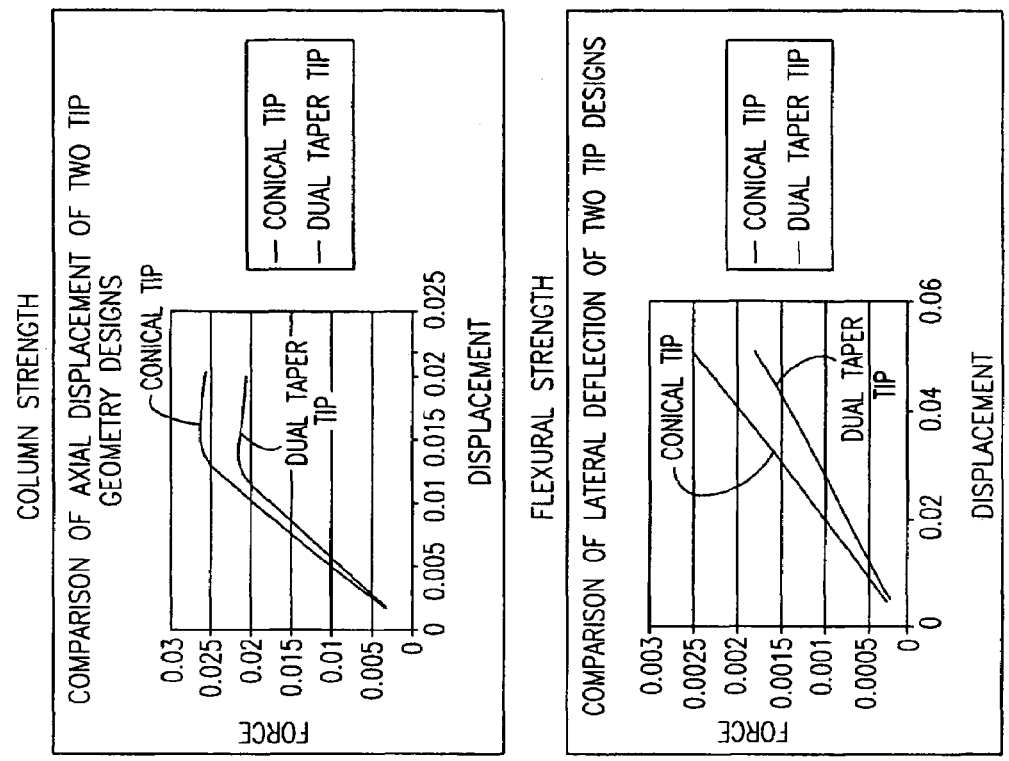
Fig. 10A
Fig. 10B
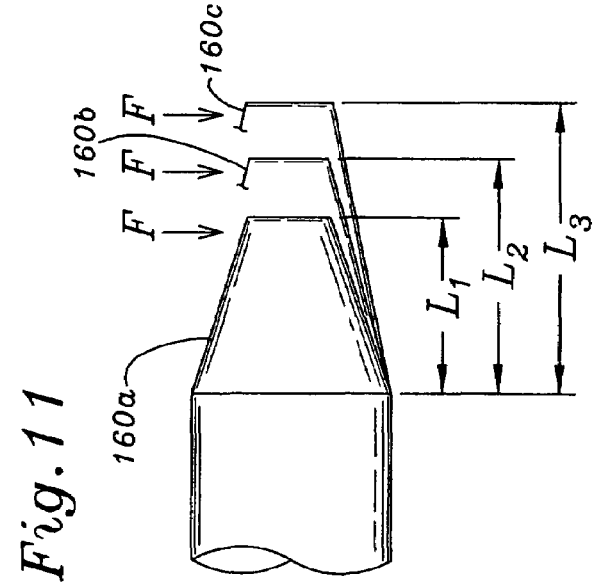
Fig. 11

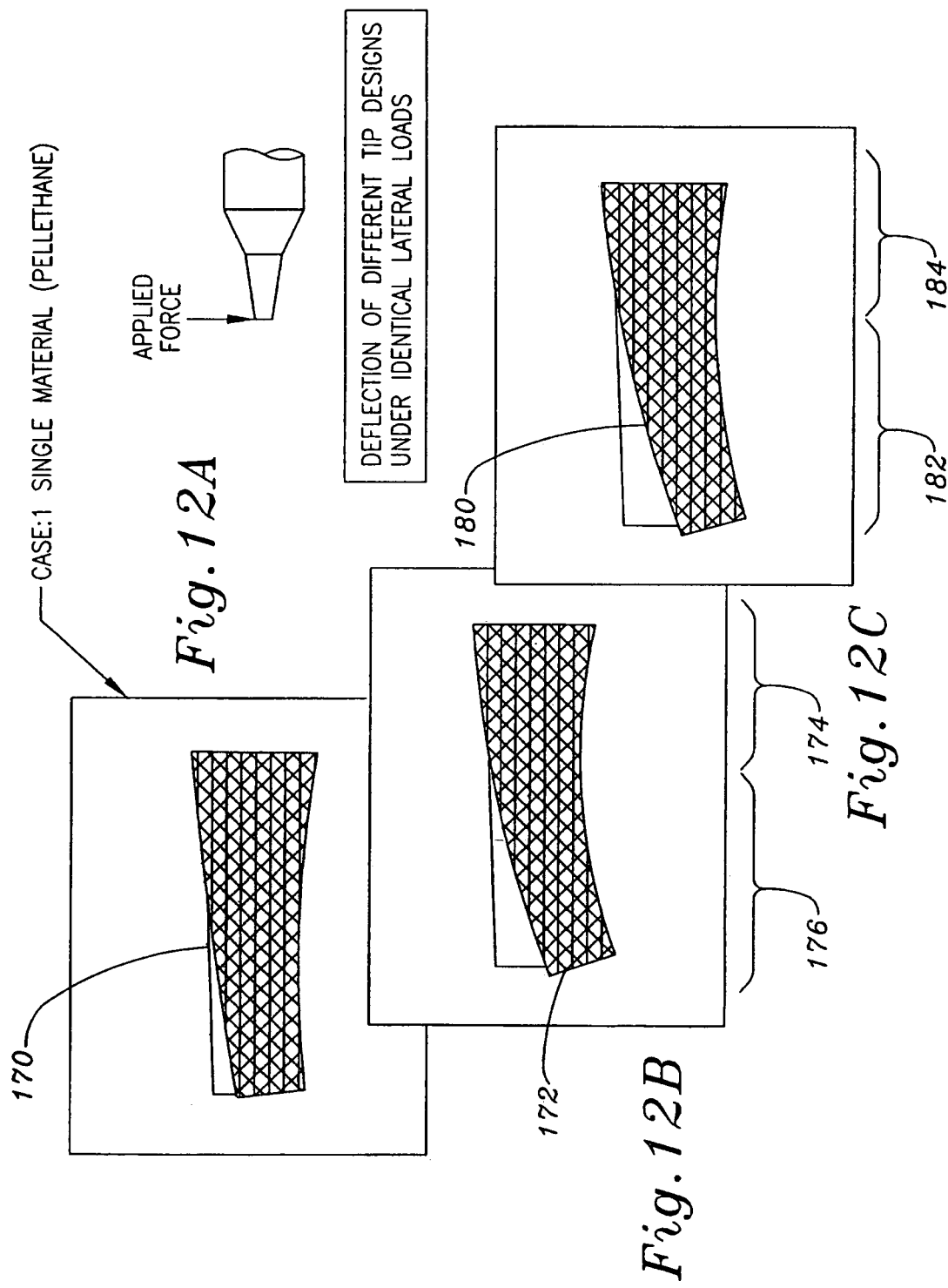

MULTIPLE LUMEN CATHETER HAVING A SOFT TIP

BACKGROUND OF THE INVENTION

The present invention relates generally to medical devices and, more particularly, to a catheter having a soft tip and multiple lumens extending through the tip for passage of devices used, for example, to measure oxygen saturation of blood.

At present, catheters that have a soft tip designed to prevent puncture of a vessel wall are exclusively single lumen catheters. In these catheters, if multiple lumens are required they are limited to the catheter body and do not extend through the distal tip. Side ports proximal to the distal tip permit the fluid to be infused from the lumens. For example, central venous (CV) catheters have a soft, single lumen tip and are used primarily to gain access to the venous vasculature for fluid infusion, blood sampling and central venous pressure monitoring. CV catheters are inserted into the patient using the Seldinger technique. This involves identifying the target vein, puncturing the vein and inserting a guidewire. A vessel dilator is inserted over the guidewire and pushed through the vessel wall to create an opening for the CV catheter. The dilator is removed though the guidewire remains in place. The single lumen CV catheter is then threaded over the guidewire and pushed through the tissue and into the vessel. Importantly, the catheter is inserted without any stiffening members other than the guidewire. The tissue and vessel wall resist the catheter as it slides into the vessel. Therefore, to insure the catheter can easily slide into the body, the catheter body and catheter tip must be sufficiently rigid to slide over the guidewire into the blood vessel without buckling or otherwise collapsing. Once a CV catheter is placed into the blood vessel, then the stiffness that was desirable during insertion through the vessel wall becomes a disadvantage. Vessel perforation is always a concern in the design of these catheters. Another concern is that the catheter tip migrates from the central vena cava to the right atrium. The right atrium contains regions of thick and thin walls. During routine monitoring, if catheter has migrated into the right atrium, through the action of normal heart beats, and lodges into the heart wall in one of the thin walls sections, the catheter tip can punch through the atrial wall and create cardiac tamponade. If the superior vena cava above the pericardial sac is perforated, a pleural infusion is created, leaking fluid into the pleural or lung cavity. During use, a stiff catheter and tip increases the possibility of endothelial abrasion and vessel wall or right atrium wall perforation. Such perforation generally requires surgical intervention to resolve.

Because of these dangers, CV catheters typically include a soft distal tip that yields when it contacts a vessel wall, and a radiopaque marker is incorporated into the tip to monitor its location within the body. This reduces, but does not eliminate, the possibility of the catheter perforating the vessel wall during repeated contact during use. Therefore, CV catheters tips have been made with softer materials to yield more easily when contacting a vessel wall. Such tips are made of materials such as low durometer urethanes, for example Tecoflex and Pellethane, due to their high durability and ease of manufacturing.

Importantly, however, all commercially available CV catheters with soft distal tips have one common feature—their distal tip has only a single lumen which is used for passing a guidewire during insertion and later during the use of the catheter may serve for fluid infusion. Such a lumen extending through the distal tip does not have any medical implement, for example, a sensor or a probe, located within because it would compromise the flexibility of the soft tip and would also interfere with the passing of the guidewire during insertion. More than one lumen in the distal tip creates an asymmetry in the transverse cross-section and increases the chances of buckling. Therefore, CV catheters are uniformly constructed with a single lumen at the distal tip. Of course, any other type of catheters that requires such a soft tip are at present single lumen, not just CV catheters.

Typical pulmonary artery (PA) catheters, on the other hand, have blunt rigid tips because they are usually inserted through a vascular access introducer. Such an introducer has already been positioned within the target vessel, and includes a large bore port through which the PA catheter can be passed, and a hemostasis valve on its proximal end to prevent blood leakage around the catheter. Such stiff, flat tips are relatively easy to manufacture and facilitate polishing of the distal end of the optical fibers. Therefore, the above described PA catheters are known to include either single or multiple lumen rigid distal tip.

As a result, at present the only catheter tips available are either single lumen soft tip or single/multiple lumen rigid tip. Accordingly, there is a need for an improved catheter having a soft tip and multiple lumens extending through the soft tip.

SUMMARY OF THE INVENTION

The present invention provides a system having a multiple lumen catheter with a soft multiple lumen tip. The catheter has a generally tubular catheter body having a proximal end and a distal end, and at least one primary lumen and at least one medical implement lumen therein. The catheter further includes a tapered catheter distal tip having a proximal end abutting the distal end of the catheter body and a distal end. The catheter tip defines at least one primary lumen aligned with the primary lumen(s) of the catheter body and at least one medical implement lumen aligned with the medical implement lumen(s) of the catheter body. A bending portion of the catheter tip is softer than the catheter body and has sufficient column strength to resist buckling during insertion, but is sufficiently flexible to deform when the tip is subjected to axial or radial loads in the body in the absence of the guidewire.

The catheter tip desirably has a proximal region and a distal region, and the distal region has a different durometer than the proximal region, or at least one of the proximal and distal regions is made of a material that has a durometer of less than or equal to 100 Shore A hardness. The distal region may be more flexible than the proximal region, or visa versa. The catheter tip may have at least two exterior tapered angles, and the proximal region may have a greater taper angle than the distal region. In transverse cross-section, both the primary lumen and the medical implement lumen may be enlarged in the proximal region relative to the surrounding material in comparison to the relative size of the lumens and material in the distal region, such that the proximal region has a larger air-to-material ratio than the distal region.

The system may further include a medical implement extending through the medical implement lumen of the catheter body and the medical implement lumen of the catheter tip. The medical implement may be one of the following: at least one optical fiber; a pH sensor; a pressure sensor; a temperature sensor; at least one pacing lead; a pacing probe; and a pacing electrode.

The medical implement may also be a sensor for measuring physiologic parameters secured to the medical implement lumen only at the distal end of the catheter tip. The sensor may be secured using adhesive that is only applied along a short portion of the medical implement lumen having an axial length of between 0.5–3.5 mm. The adhesive may be cured by ultraviolet light, and wherein a portion of the catheter tip permits passage of ultraviolet light therethrough into the medical implement lumen.

The medical implement may even be a probe that fits through the medical implement lumens of the catheter body and the catheter tip, and is removable from the catheter.

In one aspect, the soft multiple lumen catheter tip is formed of two materials. In some embodiments one material may comprises a portion that permits passage of ultraviolet light, and another material may provide a radiopaque marker. The catheter tip may have a length of at least 7.6 mm (0.30 inches) such that it is highly flexible when subjected to radial forces.

Another multiple lumen catheter having a soft tip of the present invention comprises a generally tubular catheter body having a proximal end and a distal end, the catheter body defining therein at least one primary lumen and at least one medical implement lumen. A soft, tapered distal catheter tip is provided having a proximal end abutting the distal end of the catheter body and a distal end. The catheter tip defines at least one primary lumen aligned with the primary lumen (s) of the catheter body and at least one medical implement lumen aligned with the medical implement lumen(s) of the catheter body. The catheter tip has a proximal region and a distal region, wherein at least one of the proximal and distal regions is more flexible than the catheter body.

A still further multiple lumen catheter having a soft tip of the present invention comprises a generally tubular catheter body having a proximal end and a distal end. The catheter body defines therein at least one primary lumen and at least one medical implement lumen. The catheter has a soft, tapered distal catheter tip having a proximal end abutting the distal end of the catheter body and a distal end, the catheter tip defining at least one primary lumen aligned with the primary lumen(s) of the catheter body and at least one medical implement lumen aligned with the medical implement lumen(s) of the catheter body. The catheter tip is at least partly formed of a material that has a durometer of less than or equal to 100 Shore A hardness.

BRIEF DESCRIPTION OF THE DRAWINGS

FIG. 2A is a partial sectional view of a taper-tipped prior art catheter similar to that shown in FIG. 1A traveling over a guidewire and just prior to insertion into a body vessel;

FIG. 2B is a graph generally illustrating the reaction force experienced by the operator when the inserting the catheter of FIG. 2A into the vessel;

FIG. 3A is a partial sectional view of a blunt-tipped prior art catheter traveling over a guidewire and just prior to insertion into a body vessel;

FIG. 3B is a graph generally illustrating the reaction force experienced by the operator when the inserting the catheter of FIG. 3A into the vessel;

FIG. 4 is a side elevational view of a typical pulmonary artery (PA) catheter of the prior art;

FIGS. 7A and 7B are longitudinal sectional and end elevational views, respectively, of a catheter of the present invention having a soft multiple lumen tip;

FIG. 7C is a transverse sectional view through the catheter of FIG. 7A, taken along lines 7C—7C and slightly enlarged;

FIGS. 10A and 10B are graphs comparing the axial and lateral displacements, respectively, of a standard conical tip and the dual-taper tip of FIG. 9A subject to axial and radial loads;

FIG. 11 is a schematic elevational view of a catheter tip of the present invention having various lengths for increased flexibility;

FIGS. 12A–12C are Finite Element models of three catheter tips of the present invention, all being subjected to the same lateral load;

DESCRIPTION OF THE PREFERRED EMBODIMENTS

The following detailed description, and the figures to which it refers, are provided for the purpose of describing example(s) and specific embodiment(s) of the invention only and are not intended to exhaustively describe all possible examples and embodiments of the invention.

The present invention generally relates to catheters used in the body that require a soft multiple lumen distal tip. Further, the present invention relates to any catheter, including but not limited to PA catheters, peripherally inserted catheters ("PICs"), CV catheters, or any other catheter that requires some medical implement to extend through one of the lumens of its multiple lumen tip where maintaining the softness and flexibility of the tip is important. One embodiment of the invention is described in relation to an improved central venous catheter having at least one, and preferably a plurality, of optical fibers for measuring oxygen saturation of venous blood. This description is strictly exemplary and it should be understood that various aspects of the invention by no means are limited to central venous catheters but rather generic to various catheters fitting within the above-mentioned parameters. The present invention is especially useful for catheters inserted over a guidewire using a Seldinger technique.

Furthermore, various exemplary embodiments of the present invention describe maintaining the soft, flexible nature of the multiple lumen distal tip of the catheter while a somewhat stiffer medical implement, represented by exemplary optical fibers, is extended therethrough. The invention, of course, is not limited to optical fibers, and any medical implement, examples of which are provided below, that passes through the catheter to its distal tip may be substituted.

Prior to a discussion of the various advantageous aspects of the novel catheters of the present invention, various prior art catheters will be described.

Figure 1B:
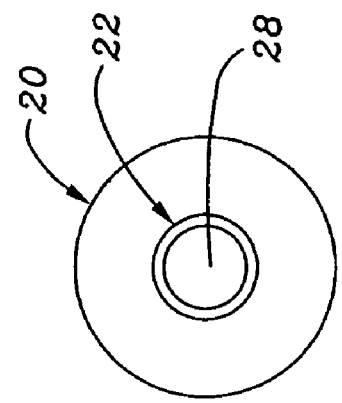
FIGS. 1A and 1B are longitudinal sectional and end elevational views, respectively, of a central venous catheter of the prior art having a single lumen tip.
Figure 1A:
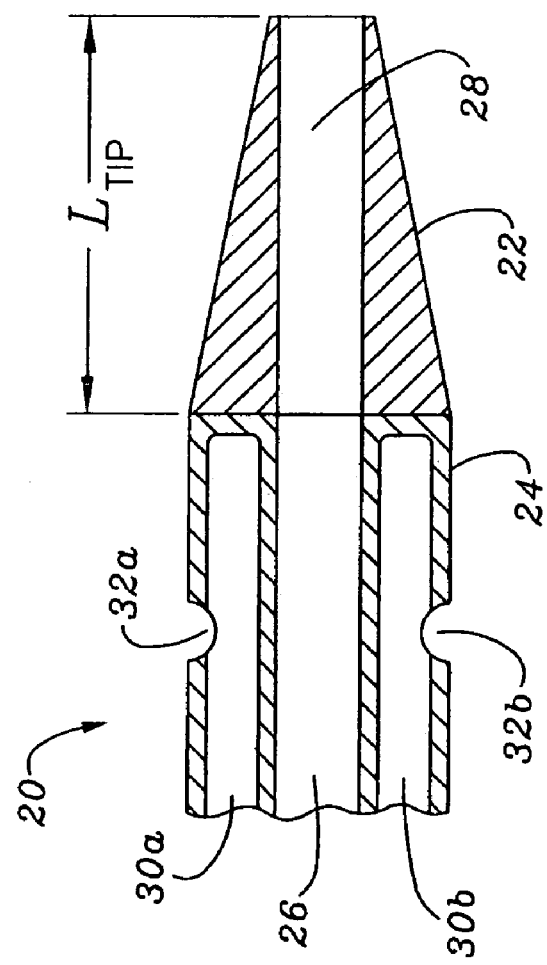

FIGS. 1A and 1B schematically illustrate the distal end of a prior art central venous catheter 20. As mentioned above, central venous catheters are introduced into the venous system using the Seldinger technique, which involves advancing the catheter 20 over a previously inserted guidewire. This will be more clearly described with respect to FIGS. 2 and 3, but catheter 20 includes a tapered, soft distal tip 22 formed on the end of, or otherwise attached to, a main catheter body 24. The length of the tip 22 is shown as $L_{TIP}$, which is typically around 6.35 mm (0.25 inches), and no more than 7.4 mm (0.29 inches). FIG. 1B is a view of the end of the catheter 20 which illustrates that the largest outer diameter of the tip 22 is as large as the outer diameter of catheter body 24.

The soft tip 22 is typically constructed separately from the catheter body 24 and attached thereto using adhesive or heat bonding. The catheter body 24 is relatively flexible so as to easily pass through curvature in the venous vasculature. Exemplary materials for the catheter body 24 include Tecoflex and Pellethane. The soft tip 22 is relatively more flexible than the body 24, and is typically made of Tecoflex.

The catheter body 24 includes a generally centered through lumen 26 that is aligned with a generally centered through lumen 28 in the soft tip 22. These aligned lumens 26, 28 permit the catheter 22 to ride over the guidewire. Furthermore, once properly inserted, the guidewire can be removed and fluid can be passed through the lumens 26, 28. The catheter body 24 further includes a pair of auxiliary lumens 30a, 30b that are shown closed at their distal ends. Each of these auxiliary lumens 30a, 30b communicates with the interior of the body vessel through a side port 32a, 32b located just proximal to the end of the catheter body 24. Therefore, fluid may be infused through the lumens 30a, 30b and side port 32a, 32b into the target vessel. Although not shown, some type of radiopaque or otherwise imageable marker is typically provided on the tip 22 for the purpose of locating the tip within the body.

It is important to note that the central venous catheter 20 has only a single lumen (aligned lumens 26, 28) that extends to the soft tip 22 which is used for passing a guidewire during insertion, and later for fluid infusion. Such a lumen extending through the distal tip 22 cannot have any medical implement, for example, a sensor or a probe, located within it because such an implement would compromise the flexibility of the soft tip and would also interfere with the passing of the guidewire during insertion.

Now with reference to FIGS. 2–4, the shapes of the distal ends of various catheters are shown in conjunction with their use. FIG. 2A shows a conventional CV catheter 20 having a tapered tip 22, such as that shown in FIGS. 1A and 1B, riding over a guidewire 40 that has previously been inserted into a body vessel 42. The guidewire 40 passes through an insertion path 44 formed in the surrounding tissue and the wall of vessel 42. Typically, this insertion path 44 is first formed with a needle and a guidewire inserted therethrough. Subsequently, a tubular instrument known as a dilator is inserted over the guidewire and pushed through the tissues surrounding the puncture hole and into the vessel. This creates a large enough opening for the tapered catheter 20. FIG. 2B is a schematic graph of the force required to push the catheter 20 through the insertion path 44. A relatively low insertion force is required to pass the catheter 20 into the vessel 42, which is preferred by the operator.

FIG. 3A shows another exemplary catheter 50 of the prior art that has a relatively blunt and rigid tip 52. The catheter 50 is shown riding over a guidewire 54 that has previously been inserted into a body vessel 56 through an insertion path 58. Forcing the blunt tip 52 through the insertion path 58 results in the insertion force graph of FIG. 3B. That is, in contrast to the graph of FIG. 2B for the tapered tip 22, the insertion force required is much larger. Disadvantageously, the higher forces are transmitted to the catheter body which may tend to buckle, and the catheter may cause trauma to the tissue surrounding the insertion path 58. Furthermore, the operator experiences difficulty in inserting the catheter 50 into the vessel 56, which is disconcerting and makes the task more difficult.

For comparison, FIG. 4 illustrates a typical prior art pulmonary artery (PA) catheter tip 60 that also includes a blunt or flat end face 62 that provides a terminus for the fiber optics therein. Because of this blunt end face 62, insertion using the Seldinger technique, as with the catheter shown in FIG. 3A, results in high insertion forces and potential damage to the surrounding tissue. The PA catheter 60 further includes a recessed region 64 near its distal end for mounting an expansion balloon, which stiffens the distal tip.

Oximetry PA catheters also has a blunt or flat distal tip which provides an interface with a calibrating media for the fiber-optics therein. Specifically, the distal end of the catheter with the fiber optics is held in contact with an in vitro calibrating device which permits calibration of the catheter without drawing a blood sample from the patient. Oximetry PA catheters include an expansion balloon on their distal end for stiffening the tip. PA catheters with rigid blunt tips are acceptable in certain applications in light of their use and certain insertion techniques. However, if it becomes desirable to use different insertion technique of these catheters, such as the Seldinger technique, the rigidity of the distal tip of such catheters will be undesirable.

There is believed to be only one commercially available central venous (CV) catheter with oximetry, available from Edwards Lifesciences of Irvine Calif. The distal end of this catheter is illustrated in FIGS. 5A–5B and 6A–6B, and includes a multi-lumen catheter body 70, a reduced diameter distal portion 72 for insertion into a calibration device, and a formed distal tip 74. The distal tip includes a flat end face 76 providing a terminus for a primary lumen 78 and a smaller fiber-optic lumen 80 housing at least two optical fibers 82. The catheter is formed of a single, homogeneous material and the reduced diameter distal portion 72 is thermo-formed on the end of the extruded catheter body 70. The forming process renders the distal portion 72 and distal tip 74 relatively rigid.

Figure 5A:
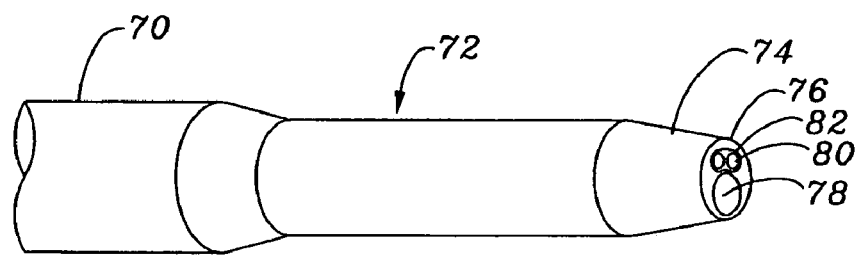
FIGS. 5A and 5B are perspective and longitudinal sectional views, respectively, of a central venous catheter of the prior art that includes fiber optics extending through a lumen to the rigid distal tip.
Figure 5B:
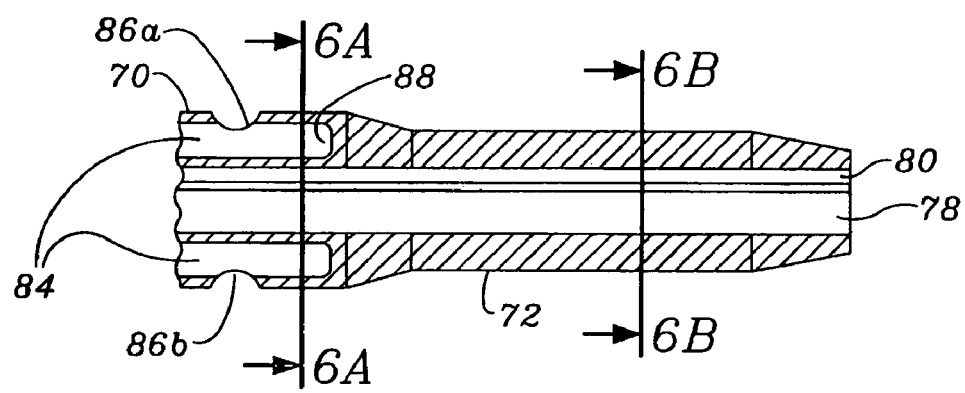
Figure 6A:
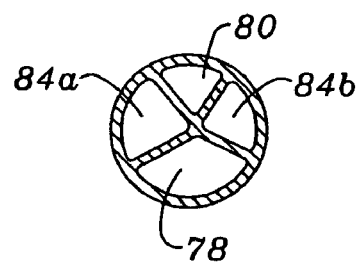
FIGS. 6A and 6B are transverse sectional views through the catheter of FIGS. 5A and 5B, taken along lines 6A—6A and 6A—6B, respectively.
Figure 6B:
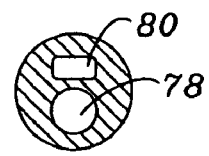

With reference to FIG. 5B and FIGS. 6A–6B, the catheter body 70 houses four lumens; the aforementioned primary lumen 78 and fiber-optic lumen 80, as well as a pair of infusion lumens 84a, 84b that open through the side wall of the catheter body 70 at a pair of side ports 86a, 86b. The infusion lumens 84a, 84b terminate at dead-end walls 88 at the distal end of the catheter body 70. Therefore, only the primary lumen 78 and fiber-optic lumen 80 extend through the entire catheter to the distal end face 76, which also contributes to rendering the distal portion 72 stiff because there is a smaller air-to-material ratio.

The CV oximetry catheter shown in FIGS. 5 and 6 is not an ideal design. Although the formed distal tip 74 is tapered, the distal end face 76 is flat to accommodate the fiber optics which results in a fairly rigid blunt tip similar to a PA catheter, such as shown in FIG. 4. The blunt rigid tip is difficult to insert into a vessel using the Seldinger technique and increases the risk of vessel perforation once in the vessel, compared to a soft tip CV catheter. As mentioned above, a preferred CV catheter has a soft, tapered distal tip.

More generally, there are three basic requirements that need to be met for a tip of any catheter where the vessel abrasion or perforation is an issue, with or without the presence of the medical implement. First, the column strength of the catheter tip should be maximized during insertion over the guidewire or similar means so as to prevent buckling. Secondly, the column strength of the catheter tip once the guidewire is removed should be minimized. More particularly, the tip should collapse easily if an axial load is applied, which is particularly important, for example, if the catheter migrates into the right atrium as could be the case for a CV catheter. Finally, the bend resistance of the catheter tip should be minimized so the tip will bend if it comes in contact with the vessel wall. Unfortunately, adding medical implement, for example, fiber optics or any other sensor or probe to a catheter distal tip normally undermines the last two flexibility requirements.

In answer to the problems of prior catheters and to present a solution meeting the above three requirements, the present invention provides a multiple lumen catheter which has a multiple lumen soft distal tip that stiff enough to resist buckling during insertion and flexible thereafter. The present invention further provides a catheter with a multiple lumen tip that meets the above requirements despite the presence of a medical implement in at least one of the lumens of the catheter that extends through the distal tip of the catheter.

FIGS. 7A–7C illustrate an exemplary a catheter 80 of the present invention which provides these features. The catheter 80 has a catheter body 88 and a catheter distal tip 82. The catheter tip 82 is tapered from a small diameter distal end face 84 outward to a relatively larger diameter proximal end face 86 that abuts an interface 89 of a catheter body 88. The catheter tip 82, or at least some portion thereof, has a softer durometer than the material of the body 88, and may be made of the same or different material. If made of a different material, the catheter tip 82 attaches to the distal end of the catheter body 88 at the interface 89 using, for example, adhesive or other bonding means. Alternatively, the tip 82 and body 88 may be made of the same material, with the tip being more flexible by virtue of a construction of thinner walls or a higher air-to-material ratio cross-section then the catheter body. Suitable materials include, but are not limited to, polyurethane, silicone, or polyvinylchloride (PVC), KRATON, or any medical grade elastomer.

For purposes of this application, the term "soft tip" (or similar terms used herein) means a catheter tip that meets all three above described requirements. As a more specific example, it means that, for instance, at least a bending portion of the tip 82 should have a Shore A hardness of less than the catheter body 88, and more particularly less than 100. Stated another way, at least a bending portion of the distal tip 82 should be sufficiently soft and flexible so as to deform or collapse when it encounters the inner wall of the vessel or the heart wall.

The catheter 80 thus has the required properties mentioned above, that is, its distal tip 82 has sufficient column strength to resist buckling during insertion, but is sufficiently flexible to deform when subjected to axial or radial loads in the absence of the guidewire and its bend resistance should be minimized. Again, it should be noted that although the catheter 80 is particularly useful as a CV catheter with oximetry, various other catheters are also within the scope of the present invention, such as pulmonary artery, peripheral axis catheters, or any other catheters used in the body that require either a soft multiple lumen distal tip or some medical implement extending through one of the lumens of its multiple lumen tip where maintaining the softness and flexibility of the tip is important.

The catheter 80 has multiple lumens, at least one of which is normally associated with infusing fluid and withdrawing blood samples, and at least one other associated with placement or positioning of a biomedical sensor or other medical implement. In the illustrated embodiment, the catheter body 88 has a primary lumen 90, a device or medical implement lumen 92, and an auxiliary lumen 94. The catheter tip 82 has a primary lumen 96 and a device lumen 98. Both the primary and device lumens 90, 92 in the catheter body 88 align with the primary and device lumens 96, 98 and extend through the catheter tip 82 and open at the distal end face 84. The aligned device lumens 92 and 98 and the aligned primary lumens 90 and 96 could be alternatively described as a single device lumen extending through the catheter body and the catheter tip and as a single primary lumen extending through the catheter body and the catheter tip, respectively. In contrast, the auxiliary fluid lumen 94 terminates at the distal end of the catheter body 88 and opens at a side port 100.

In the illustrated embodiment, a medical implement is a biomedical sensor extending through the device lumens 92, 98 which comprises, as an example, one or more optical fibers 102 used to transmit and receive light for measuring oxygen saturation. In other configurations within the scope of the present invention, the device lumens 92, 98 may be used to pass various other medical implements or sensors, for example, temperature sensors, or pressure sensors, or pH sensors, or pacing leads, or pacing electrodes, or probes. FIGS. 7A–7C illustrate the transverse cross-section of the catheter tip 82, and it can be seen that the primary lumen 96 intersects the central axis of the catheter 80 but is offset in one direction with respect thereto. The device lumen 98 is shown elongated and arcuate, although other configurations, dimensions, shapes and relative positions of both lumens 96 and 98 are possible and within the scope of the present invention. Moreover, the catheter of the present invention may have additional lumens, some of which may terminate like the lumen 94 at a side port proximally to the distal tip while others may also extend through the catheterdistal tip 82. Furthermore, the catheter body 88 of the present invention may have only a device lumen 92 and a primary lumen 90 (aligned with the corresponding device lumen 98 and the primary lumen 96 of the distal tip), without an auxiliary lumen 94.

The optical fibers 102 (or other above-mentioned medical implements) are desirably fastened or secured within the distal tip 82 so as to prevent their migration. Another aspect of the present invention is that the fibers 102 are secured in a manner that does not compromise the flexibility and other required features of the soft tip 82. For example, the device lumen 98 is shown tapering down from toward the distal end face 84 tapering down from the interface 89 or proximal end of the catheter tip (which is the region adjacent to and incorporating the proximal end face 86) toward the distal end of the catheter tip (which is the region adjacent to and incorporating the distal end face 84). A short portion 104 of the device lumen 98 at a distal end of the catheter tip extending proximally from the distal end face 84 does not need to taper, but is rather sized just larger than the diameter of the fibers 102. Only in this portion 104 are the fibers 102 secured to the catheter tip 82, for example, by adhesive. Because the portion 104 is limited in axial length, the length along which adhesive or other means for attachment is provided is also limited. Preferably, the portion 104 extends axially along a length which is less than 3.5 mm, more preferably between 0.5–3.5 mm, and most preferably between 1–2 mm.

Typical adhesives used in this context are relatively stiff when cured, and other methods of securement contemplated, such as solvent bonding, heat forming, ultrasonic bonding, also result in a stiff section where applied. Even a simple compression fit results in a stiff portion where the tip 82 and fibers 102 are in interfering contact. Consequently, the combination of the joined optical fibers 102, adhesive (or other joining tehnique) applied in the prior art along all or a substantial length of the distal tip 82, and material of the distal tip 82 was significantly stiffer and did not fulfill the goals of the catheter of the present invention. Further, if not managed, bending of the region in which the adhesive was applied could cause the adhesive to crack or otherwise loosen. With the catheter of the present invention, however, because the optical fibers 102 are only secured in this short portion 104 of the device lumen 98, the remainder of the outer fibers remain free to slide with respect to the device lumens 92 or 98. Therefore, when an axial or radial load is imparted to distal tip 82, the tip deforms or buckles in the region that is proximal to this short portion 104. The very distal end of the tip 82 is relatively stiffer, but this does not compromise the performance characteristics of the catheter as mentioned above.

Figure 8B:
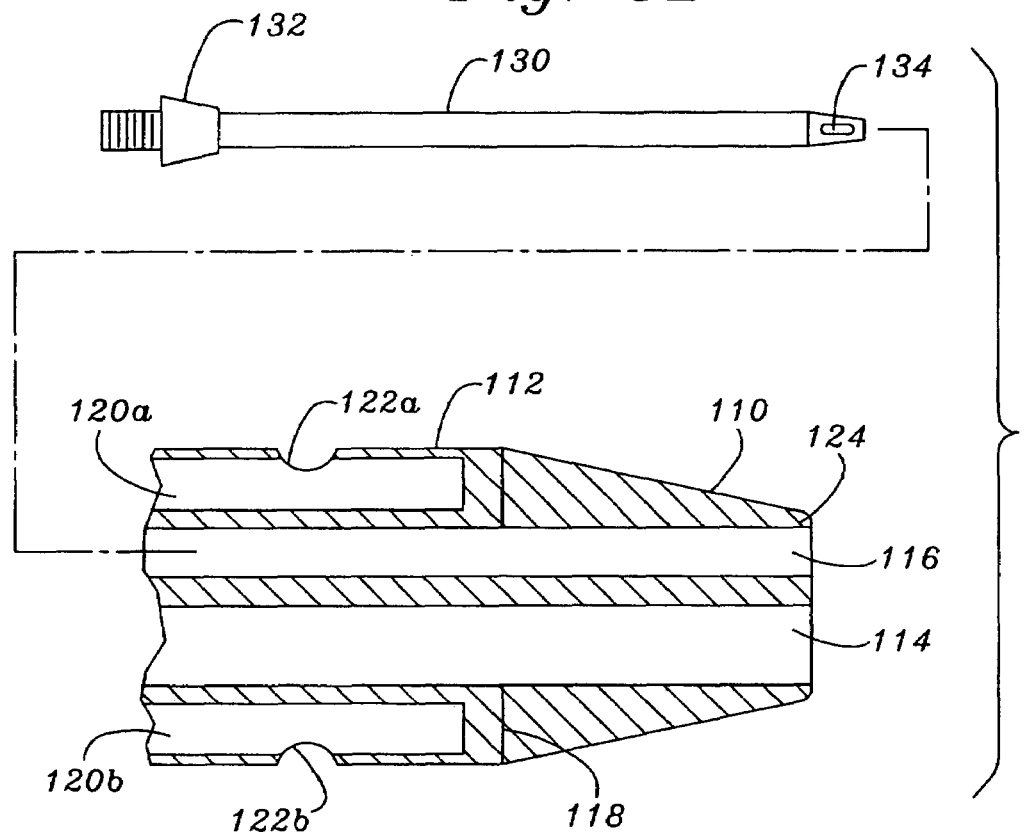
FIG. 8B is an exploded, partial sectional view of the catheter distal tip of FIG. 8A and a sensor probe used therewith.
Figure 8A:
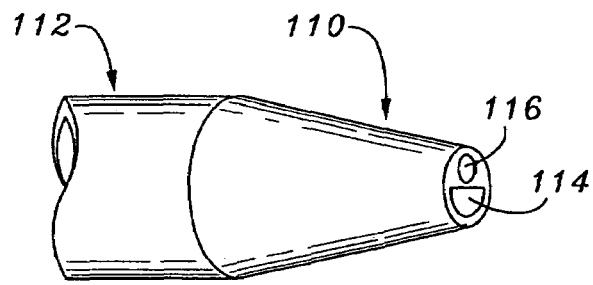
FIG. 8A is a perspective view of a soft multiple lumen distal tip of an alternative catheter of the present invention.

FIG. 8A is a perspective view of an alternative soft multiple lumen catheter tip 110 on the end of the catheter body 112 of the present invention that does not have a sensor fixed therein, such as the fiber optics 102 disclosed above. Instead, the soft distal tip 110 includes a primary lumen 114 and a device lumen 116 that receives sensors. FIG. 8B is a longitudinal sectional view of the soft distal tip 110 and catheter body 112 that are either secured together at an interface 118, or formed of a homogeneous material. The primary lumen 114 and the device lumen 116 are aligned with or continuations of similar lumens in the catheter body 112 as shown. A pair of auxiliary lumens 120a, 120b that each opens at side ports 122a, 122b may be provided in the catheter body 112. FIG. 8B also shows an elongated probe 130 that has a connector 132 at its proximal end and a sensor 134 at its distal end. The probe 130 is sized to pass through the device lumen 116 and may be utilized at or near the distal face 124 of the catheter tip 110. Sensors that can be used include fiber-optics, temperature sensors, pH sensors, pressure sensors, a sensor for cardiac pacing, and the like. Once again, because the distal tip 110 is soft (i.e., softer than catheter body 112), and because the probe 130 is not secured within the device lumen 116, the soft distal tip easily deforms upon application of axial or radial forces.

As mentioned above, the various distal tips of the catheters of the present invention are made softer than the main catheter body, and preferably soft enough to easily deform upon contact with the surrounding vessel wall or heart wall. To do this, the distal tips are made of a soft material and/or are constructed in a way that they flex easily.

Figure 9A:
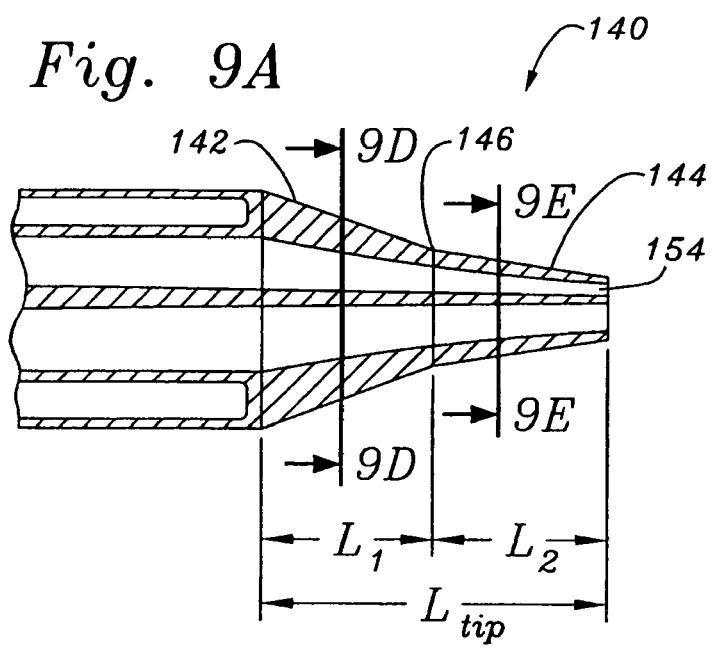
FIGS. 9A and 9B are longitudinal sectional and end elevational views, respectively, of an alternative soft multiple lumen catheter tip of the present invention having multiple tapers.
Figure 9B:
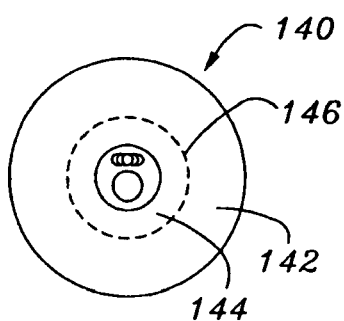
Figure 9C:
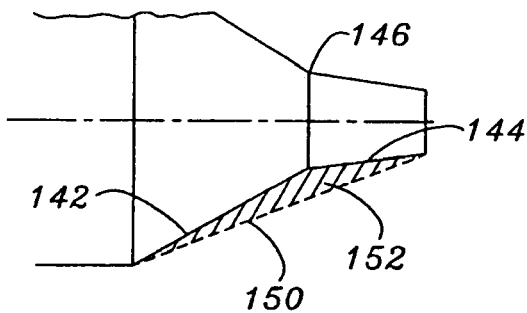
FIG. 9C is a schematic elevational view illustrating material removed from the exterior of the catheter tip of FIG. 9A so as to form the multiple tapers and create a bending focal point.
Figure 9D:
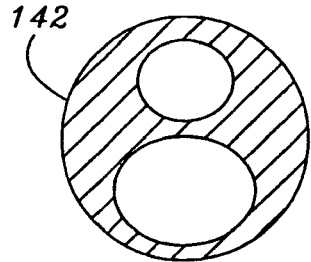
FIGS. 9D and 9E are transverse sectional views through the catheter of FIG. 9A, taken along lines 9D—9D and 9E—9E, respectively.
Figure 9E:
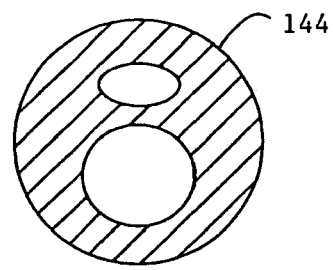

For example, FIGS. 9A–9E illustrate a soft catheter tip 140 that has a tapered proximal region 142 and distal region 144 that has a narrower taper, the two regions meeting at an elbow 146. FIG. 9D is a section through the proximal region 142, and FIG. 9E is a section through the distal region 144. The length of the proximal region 142 is shown as $L_1$, while the length of distal region 144 is shown as $L_2$. The total length of the distal tip 140 is given as $L_{TIP}$. In an exemplary embodiment, $L_{TIP}$ is about 7.6 mm (0.30 inches), and $L_1$ and $L_2$ are approximately equal. Alternatively, $L_1$ and $L_2$ may be unequal with the longer of the two lengths being preferably more flexible than the other. The exemplary taper angle of the proximal region 142 is about 30°, while the exemplary taper angle of the distal region 144 is about 15°. Other angles of taper are also within the scope of the present invention.

FIG. 9C is a schematic view of the distal tip showing in phantom the line 150 of a tip having a single taper. The cross-hatched region 152 is the volume of material that is removed to result in the differing tapers of the proximal region 142 and distal region 144. The reduction of the overall material in the center of the tip allows for a bending focal point.

FIGS. 9D and 9E illustrate the respective air-to-material ratios in the proximal region 142 and the distal region 144. As seen, there is a greater volume of air to material in the proximal region 142 than in the distal region 144. Therefore, the bending stiffness of the proximal region is less than that of the distal region. As a result, axial or radial forces imparted to the distal end face 154 of the tip 140 will cause bending in the proximal region 142 rather than in the distal region 144. Because of this, sensors placed through, or fixed in a device lumen 156, are positioned within a relatively stiff distal region which is beneficial in some instances, such as when calibrating fiber optics.

Alternatively, rather than removing material from the exterior of the distal tip 140, the lumens 156 and 158 may be enlarged within the tip to result in the same effect. That is, more material may be removed to enlarge the lumens in the proximal portion 142 to create a larger air-to-material ratio therein. This is shown further in FIGS. 13A–13C. Of course, various combinations of the two can also be utilized.

FIGS. 10A and 10B are graphs that illustrate the column strength and flexural strength, respectively, of the standard conical tip and a dual-tapered tip, such as that shown in FIG. 9A. In both graphs, the applied force in pounds is indicated at the left along the vertical axis, while the corresponding displacement of the respective tips in inches is shown along the horizontal axis. As indicated, the dual-tapered tip displaces farther in either case at lower applied forces. This means that the dual-tapered tip more easily buckles upon an applied axial force and bends more easily upon an applied radial force.

FIG. 11 schematically illustrates several superimposed soft catheter distal tips 160a, 160b, 160c having gradually longer lengths L1, L2, L3, respectively. Each of these tips 160 has a single conical taper and is otherwise cylindrical and configured much like previously described catheter distal tips. A radial force F is shown applied near the distal end of each of the tabs. One way to render the tip more flexible is to increase its length. Therefore, the longest tip 160c will bend the farthest distance from the implied force F because of the longer lever arm. For multiple lumen soft catheter tips of the present invention, the length should be at least 5.1 mm (0.20 inches), and preferably at least about 7.6 mm (0.30 inches). An additional benefit of increasing the length of the distal tip is that the taper angle is reduced, which reduces the resistance to insertion using the Seldinger technique, and consequently reduces the required column strength of the distal tip.

FIGS. 12A–12C are Finite Element models of different catheter tips of the present invention, each under the same radial or lateral load. FIG. 12A shows a deflected tip 170 that is made of a single homogeneous material, and the corresponding relaxed state is seen in phantom. FIG. 12B shows a tip 172 that has a proximal region 174 made of the same material as the entire tip 170 in FIG. 12A, and a distal region 176 made of a softer material (i.e., more flexible). Accordingly, the distal region 176 curls and deflects more than the distal portion of tip 170 in FIG. 12A. Finally, FIG. 12C illustrates a tip 180 that has a distal region 182 made of the same material as the entire tip 170 in FIG. 12A, and a proximal region 184 made of a softer material (i.e., more flexible). Therefore, under load, the tip 180 bends more than tip 170 in FIG. 12A. The behavior of tip 180 under a lateral load approximates that of the tips discussed above that have optical fibers glued to their distal ends, thus making the distal region more stiff than the proximal region. The lengths of the regions may be equal or not, and the tips may be made from the various material discussed herein, such as Pellethane and Tecothane, both urethanes. The softer of the two materials, or in other words the bending portion, preferably has a durometer of less than 100 Shore A, more particularly between about 45–100 Shore A, most desirably about 75 Shore A.

Figure 13A:
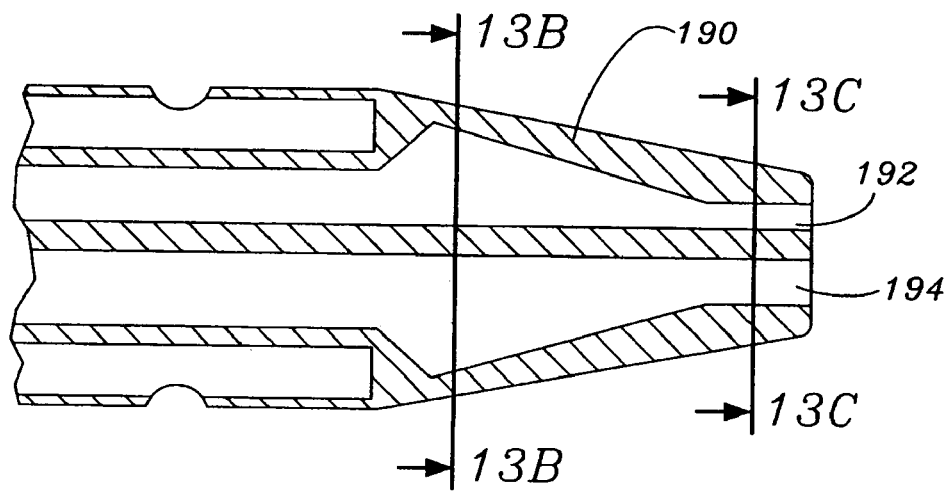
FIG. 13A is a longitudinal sectional view through a catheter distal tip of the present invention.
Figure 13B:
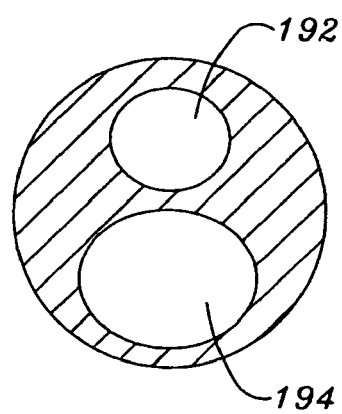
FIGS. 13B and 13C are transverse sectional views through the catheter of FIG. 13A, taken along lines 13A—13B and 13C—13C, respectively, illustrating the different cross-sectional areas of primary and device lumens at those two locations.
Figure 13C:
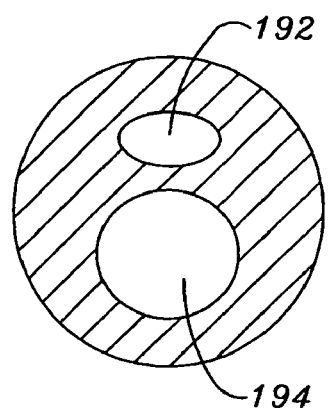

FIGS. 13A–13C illustrate a further configuration for rendering a portion of the catheter distal tip more soft and flexible than the rest of the catheter body. Specifically, FIG. 13A shows the distal tip 190 having a proximal region shown in cross-section in FIG. 13B and a distal region shown in cross-section in FIG. 13C. As can be seen, a device lumen 192 and a primary lumen 194 are reduced in size in the distal region shown in FIG. 13C. This means that the air-to-material ratio in the distal region is less than that in the proximal region, and thus the distal tip 190 bends or buckles in the proximal region. Another alternative embodiment of the present invention may combine a dual-taper tip of the catheter with the different materials of various portions of the distal tip. One exemplary configuration of the dual-material, dual-taper is where the proximal segment consists of a high durometer material while the distal segment consists of a lower durometer material. This configuration creates a very flexible tip with low column strength.

Figure 14A:
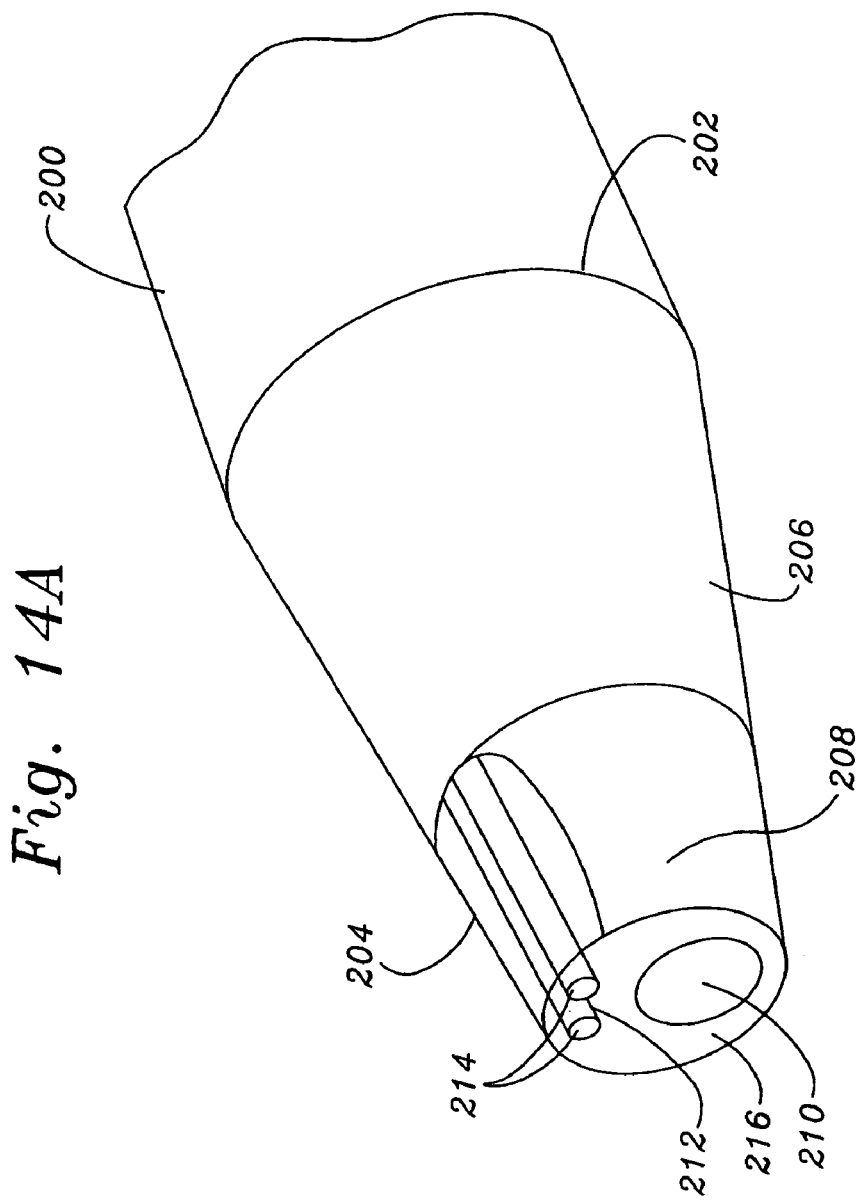
FIG. 14A is perspective view of an alternative catheter distal tip of the present invention made of two materials.

A further example of a soft-tipped catheter of the present invention is seen in FIG. 14A. In this aspect of the present invention, a catheter body 200 attaches at an interface 202 to a distal tip 204 formed of two materials. A proximal region 206 of the catheter tip 204 is formed of a first material and a distal region 208 of the catheter tip is formed of a second material. In this embodiment, the catheter tip includes a primary lumen 210 and a device lumen 212. By way of example and not limitation, a medical implement, such as a pair of optical fibers 214, extend through the device lumen 212. As before with reference to FIG. 7, the fibers could be secured by adhesive and the adhesive could be applied only along a short portion adjacent the distal face 216, and preferably along a portion between 0.5–3.5 mm in length.

The two materials of the proximal and distal regions 206, 208 may be more or less relatively flexible depending on the catheter tip design. For example, if a sensor such as fiber optics is secured in the distal end of the tip, the proximal region is desirably more flexible (softer) so that it provides a point of bending. Various combinations of materials such as polyurethane, silicone, or polyvinylchloride (PVC), KRATON, or any medical grade elastomer may be used to create a catheter tip that is either more flexible in the proximal region or more flexible in the distal region. Furthermore, various constructional differences may accentuate the difference in flexibility.

Figure 14B:
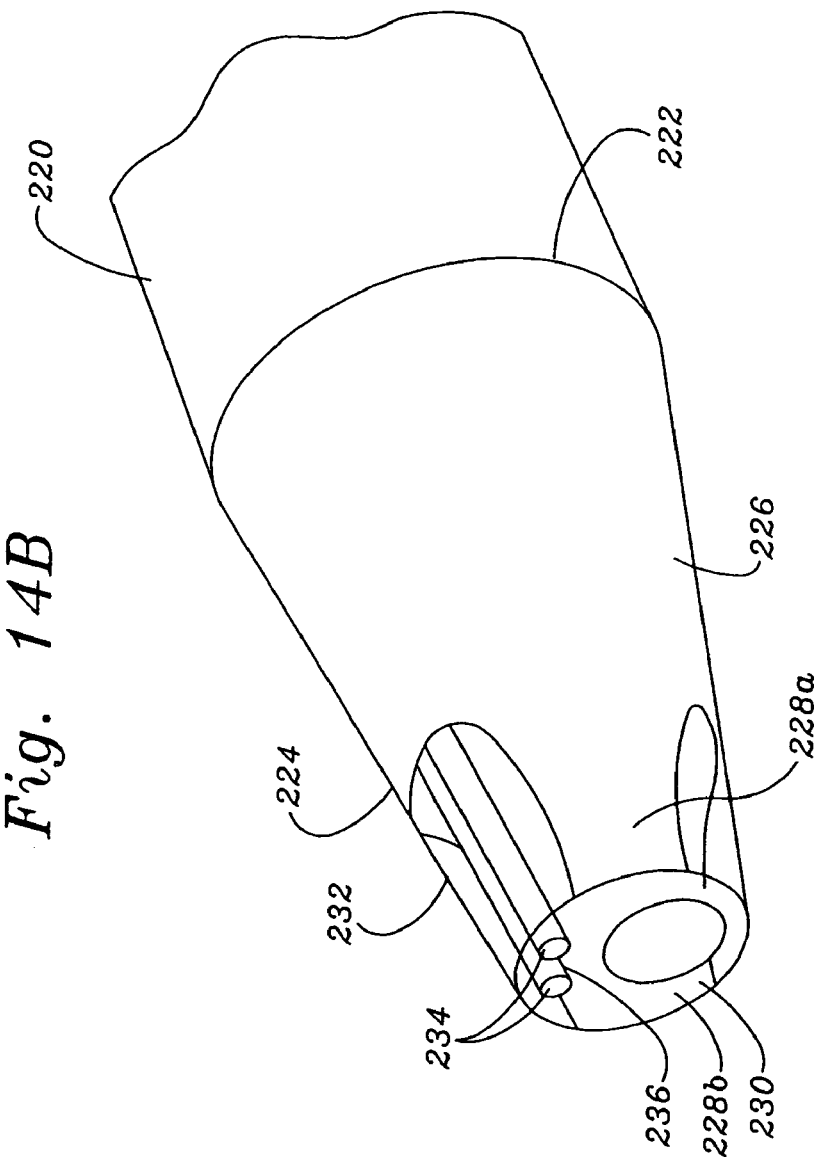
FIG. 14B is a perspective view of another alternative catheter distal tip of the present invention, that facilitates attachment of optical fibers in a device lumen at a distal end of the catheter tip.

FIG. 14B illustrates a still further alternative configuration of a catheter distal tip of the present invention. As in FIG. 14A, a catheter body 220 attaches at an interface 222 to a distal tip 224 formed of two materials. In this embodiment, however, a first material 226 forms a proximal region and two generally axially-oriented segments 228a, 228b thereof extend on diametrically opposed sides of the distal tip all the way to a distal face 230. Of course, more than two generally axially-oriented segments, similar to 228a and 228b, are within the scope of the present invention. A second material 232, which could be transparent, fills the remainder of the spaces between two or more segments 228a, 228b. Optical fibers 234 extend through a device lumen 236 and are secured therein with adhesive. As before, the adhesive is only applied along a short portion adjacent the distal face 230, and preferably along a portion between 0.5–3.5 mm in length.

The second material 232 may be transparent or only partly opaque such that ultraviolet light can pass therethrough. A suitable adhesive is one that is cured with ultraviolet light, and the first material 226 is desirably opaque to prevent such light passing through. In this manner, adhesive can be injected into the device lumen 236, and upon application of ultraviolet light, only a portion that is exposed by the first material 226 becomes cured. This reduces the importance of the volume of adhesive injected into device lumen 236, and thus facilitates assembly and ensures consistency.

The transparent material 232 in the distal tip provides a window through which ultraviolet light can pass and cure adhesive previously injected into the device lumen 236. The first material 226 may be radiopaque such that the side segments 228a, 228b provide axially-oriented markers to guide positioning of the distal tip 224 within the body.

In assembling the catheter tips of FIGS. 14A and 14B, the dual-material distal tips and catheter body may be constructed using an RF tip forming process, but techniques such as heat forming or steam forming may also work. This involves the use of three extruded tubes, one for the catheter body, and two others for the dual-material tip. Two mandrels are inserted through the three tubes and RF tip formed simultaneously. Once the catheter is constructed, the adhesive is drawn into the device lumen using a vacuum pump. If the transparent materials are used in the tips, they would provide an advantage in that the depth of the adhesive can be visualized. Another alternative is to do without the transparent material but instead use an opaque or semi-opaque material that still permits some ultraviolet light through, and which may be entirely radiopaque. An adhesive that can be cured by ultraviolet light or heat could be used.

Some ultraviolet passes through the tip material and partially cures the adhesive, and the remainder of the curing process is done using heat.

It will be appreciated that the invention has been described hereabove with reference to certain examples or preferred embodiments as shown in the drawings. Various additions, deletions, changes and alterations may be made to the above-described embodiments and examples without departing from the intended spirit and scope of this invention. Accordingly, it is intended that all such additions, deletions, changes and alterations be included within the scope of the following claims.

What is claimed is:

1. A system having a multiple lumen catheter with a soft tip, comprising:
    a generally tubular catheter body having a proximal end and a distal end, the catheter body defining therein at least one primary lumen and at least one medical implement lumen; and
    a tapered catheter distal tip having a proximal region and a distal region, a proximal end abutting the distal end of the catheter body and a distal end, the catheter tip defining at least one primary lumen aligned with the primary lumen(s) of the catheter body end at least one medical implement lumen aligned with the medical implement lumen(s) of the catheter body, wherein a bending portion of the catheter tip is softer than the catheter body and has sufficient column strength to resist buckling during insertion, but is sufficiently flexible to deform when the tip is subjected to axial or radial loads in the body in the absence of the guidewire, and wherein, in transverse cross-section, both the primary lumen and the medical implement lumen are enlarged in the proximal region relative to the surrounding material in comparison to the relative size of the lumens and material in the distal region, such that the proximal region has a larger air-to-material ratio and is more flexible than the distal region.

2. The system of claim 1, further including:
    a medical implement extending through the medical implement lumen of the catheter body and the medical implement lumen of the catheter tip.

3. The system of claim 2, wherein the medical implement is a sensor for measuring physiologic parameters secured to the medical implement lumen only at the distal end of the catheter tip.

4. The system of claim 3, wherein the sensor is secured using adhesive that is only applied along a short portion of the medical implement lumen having an axial length of between 0.5–3.5 mm.

5. The system of claim 4, wherein the adhesive is cured by ultraviolet light, and wherein a portion of the catheter tip permits passage of ultraviolet light therethrough into the medical implement lumen.

6. The system of claim 2, wherein the medical implement is selected from the group consisting of:
    at least one optical fiber;
    a pH sensor;
    a pressure sensor;
    a temperature sensor;
    at least one pacing lead;
    a pacing probe; and
    a pacing electrode.

7. The system of claim 2, wherein the medical implement is a probe that fits through the medical implement lumens and is removable from the catheter.

8. The system of claim 1, wherein the catheter tip has at least two exterior tapered angles.

9. The system of claim 8, wherein the proximal region has a greater taper angle than the distal region.

10. The system of claim 1, wherein the catheter tip is formed of two materials.

11. The system of claim 10, wherein one material comprising a portion that permits passage of ultraviolet light, and another material that provides a radiopaque marker.

12. The system of claim 1, wherein the catheter tip has a proximal region and a distal region, and wherein the distal region has a different durometer than the proximal region.

13. The system of claim 1, wherein the catheter tip has a proximal region and a distal region, and wherein at least one of the proximal and distal regions is made of a material that has a durometer of less than or equal to 100 Shore A hardness.

14. The system of claim 1, wherein the catheter tip has a length of at least 76 mm (0.30 inches) such that it is highly flexible when subjected to radial forces.

15. A multiple lumen catheter having a soft tip, comprising:
    a generally tubular catheter body having a proximal end and a distal end, the catheter body defining therein at least one primary lumen and at least one medical implement lumen; and
    a soft, tapered distal catheter tip having a proximal end abutting the distal end of the catheter body and a distal end, the catheter tip defining at least one primary lumen aligned with the primary lumen(s) of the catheter body and at least one medical implement lumen aligned with the medical implement lumen(s) of the catheter body, wherein the catheter tip has a proximal region and a distal region, wherein the proximal region has a larger air-to-material ratio in transverse cross-section than the distal region such that the proximal region is more flexible than the distal region, and at least one of the proximal and distal regions is more flexible than the catheter body.

16. The multiple lumen catheter of claim 15, further including: a medical implement extending through the medical implement lumen of the catheter body and the medical implement lumen of the catheter tip.

17. The multiple lumen catheter of claim 16, wherein the medical implement is a sensor for measuring physiologic parameters secured to the medical implement lumen only at the distal end of the catheter tip.

18. The multiple lumen catheter of claim 17, wherein the sensor is secured using adhesive that is only applied along a short portion of the medical implement lumen having an axial length of between 0.5–3.5 mm.

19. The multiple lumen catheter of claim 18, wherein the adhesive is cured by ultraviolet light, and wherein a portion of the catheter tip permits passage of ultraviolet light therethrough into the medical implement lumen.

20. The multiple lumen catheter of claim 16, wherein the medical implement is selected from the group consisting of:
    at least one optical fiber;
    a pH sensor;
    a pressure sensor;
    a temperature sensor;
    at least one pacing lead;
    a pacing probe; and
    a pacing electrode.

21. The multiple lumen catheter of claim 15, wherein the catheter tip has at least two exterior taper angles.

22. The multiple lumen catheter of claim 21, wherein the proximal region has a greater taper angle than the distal region.

23. The multiple lumen catheter of claim 15, wherein at least one of the proximal and distal regions is made of a material that has a durometer of less than or equal to 100 Shore A hardness.

24. The multiple lumen catheter of claim 15, wherein, in transverse cross-section, both the primary lumen and the medical implement lumen are enlarged in the proximal region relative to the surrounding material in comparison to the relative size of the lumens and material in the distal region, such that the proximal region has a larger air-to-material ratio than the distal region.

25. The multiple lumen catheter of claim 15, wherein the catheter tip is formed of two materials.

* * * * *